United States Patent
Sullenger et al.

(10) Patent No.: US 7,045,293 B2
(45) Date of Patent: *May 16, 2006

(54) ALTERATION OF SEQUENCE OF A TARGET MOLECULE

(75) Inventors: Bruce Sullenger, Westminster, CO (US); Thomas R. Cech, Boulder, CO (US)

(73) Assignee: The Regents of the University of Colorado, Boulder, CO (US)

( * ) Notice: Subject to any disclaimer, the term of this patent is extended or adjusted under 35 U.S.C. 154(b) by 53 days.

This patent is subject to a terminal disclaimer.

(21) Appl. No.: 10/799,535

(22) Filed: Mar. 12, 2004

(65) Prior Publication Data

US 2004/0171058 A1    Sep. 2, 2004

Related U.S. Application Data

(63) Continuation of application No. 09/165,514, filed on Oct. 2, 1998, now Pat. No. 6,897,016, which is a continuation of application No. 08/786,753, filed on Jan. 24, 1997, now Pat. No. 5,869,254, which is a continuation of application No. 08/152,450, filed on Nov. 12, 1993, now Pat. No. 5,667,969.

(51) Int. Cl.
*C12Q 1/68* (2006.01)
*C12P 19/34* (2006.01)
*C07H 21/02* (2006.01)

(52) U.S. Cl. ............................ 435/6; 435/5; 435/91.1; 514/44; 536/23.1; 536/24.1; 536/24.5; 536/25.1

(58) Field of Classification Search .................... 435/6; 514/44; 536/24.5, 23.1
See application file for complete search history.

(56) References Cited

U.S. PATENT DOCUMENTS

| | | | |
|---|---|---|---|
| 4,987,071 A | 1/1991 | Cech et al. | |
| 5,126,260 A | 6/1992 | Tuan et al. | |
| 5,225,337 A | 7/1993 | Robertson | |
| 5,389,514 A | 2/1995 | Taylor | |
| 5,498,531 A | 3/1996 | Jarrell | |
| 5,641,673 A | 6/1997 | Haseloff et al. | |
| 5,667,969 A | 9/1997 | Sullenger | |
| 5,869,254 A | 2/1999 | Sullenger | |
| 6,897,016 B1 * | 5/2005 | Sullenger et al. ............... | 435/6 |

FOREIGN PATENT DOCUMENTS

| | | |
|---|---|---|
| EP | 90/01731 | 5/1990 |
| WO | 88/04300 | 6/1988 |
| WO | 92/07065 | 8/1992 |
| WO | 92/13089 | 8/1992 |
| WO | 92/13090 | 8/1992 |
| WO | 93/00833 | 5/1993 |

OTHER PUBLICATIONS

Goyette et al (Mol. Cell. Biol. (1992) 12(3):1387-1395).*

Weber et al., "Antiviral properties of a dominant negative mutant of the herpes simplex virus type 1 regulatory protein ICP0," *Journal of General Virology* 73:2955-2961 (1992).

Rossi, "Controlled, targeted, intracellular expression of ribozymes: progress and problems," *TIBTECH* 13:301-306 (1995).

Komatsu et al., "Cross-ligation and exchange reactions catalyzed by hairpin ribozymes," *Nucleic Acids Research* 21:185-190 (1993).

Friedman et al., "Expression of a truncated viral *trans*-activator selectively impedes lytic infection by its cognate virus," *Nature* 335:452-454 (1988).

Flanegan and Cech, "Tetrahymena Ribozyme Catalyzes Trans-splicing of Model Oligoribonucleotide Substrates," J. Cell. Biochem, 12D, Apr. 4, 1998, New York, p. 28.

Cech, "The Chemistry of Self-Splicing RNA and RNA Enzymes," *Science* 236:1532-1539 (1987).

Sullenger and Cech, "Ribozyme-mediated repair of defective mRNA by targeted trans-splicing," *Nature* 371:619-622 (1994).

Guthrie, "Messenger RNA Splicing in Yeast: Clues to Why the Spliceosome Is a Ribonucleoprotein," *Science* 253:157-163 (1991).

Kim and Cech, "Three-dimensional model of the active site of the self-splicing rRNA precursor of *Tetrahymena*," *Proc. Natl. Acad. Sci. USA* 84:8788-8792 (1987).

Haseloff and Gerlach, "Simple RNA Enzymes with New and Highly Specific Endoribonuclease Activities," *Nature* 334:585-591 (1988).

Cech, "Ribozymes and Their Medical Implications," *JAMA* 260:3030-3034 (1988).

Jeffries and Symons, "A Catalytic 13-mer Ribozyme," *Nucleic Acids Research* 17:1371-1377 (1989) (also referred to as Jefferies).

(Continued)

*Primary Examiner*—Jeffrey Fredman
(74) *Attorney, Agent, or Firm*—McDonnell Boehnen Hulbert & Berghoff LLP

(57) ABSTRACT

Method for splicing a target nucleic acid molecule with a separate nucleic acid molecule. Such splicing generally causes production of a chimeric protein with advantageous features over that protein naturally produced from the target nucleic acid prior to splicing. The method includes contacting the target nucleic acid molecule with a catalytic nucleic acid molecule including the separate nucleic acid molecule. Such contacting is performed under conditions in which at least a portion of the separate nucleic acid molecule is spliced with at least a portion of the target nucleic acid molecule to form a chimeric nucleic acid molecule. In this method, the catalytic nucleic molecule is chosen so that it is not naturally associated with the separate nucleic acid molecule.

5 Claims, 8 Drawing Sheets

OTHER PUBLICATIONS

Rossi et al., "Ribozymes as Anti-HIV-1 Therapeutic Agents: Principles, Applications, and Problems," *Aids Research and Human Retroviruses* 8:183-189 (1992).

Hampel and Tritz, "RNA Catalytic Properties of the Minimum (-)sTRSV Sequence," *Biochemistry* 28:4929-4933 (1989).

Hampel et al., "Hairpin' Catalytic RNA Model: Evidence for Helices and Sequence Requirement for Substrate RNA," *Nucleic Acids Research* 18:299-304 (1990).

Perrotta and Been, "Cleavage of Oligoribonucleotides by a Ribozyme Derived from the Hepatitis δ Virus RNA Sequence," *Biochemistry* 31:16-21 (1992).

Guerrier-Takada et al., "The RNA Moiety of Ribonuclease P Is the Catalytic Subunit of the Enzyme," *Cell* 35:849-857 (1983).

Inoue et al., "Intermolecular Exon Ligation of the rRNA Precursor of Tetrahymena: Oligonucleotides Can Function as a 5' Exons," *Cell* 43:431-437 (1985).

Bruzik et al., "Spliced leader RNAs from Lower eukaryotes are *trans*-spliced in mammalian cells," *Letters to Nature* 360:692-695 (1992).

Cech et al., "*In Vitro* Splicing of the Ribosomal RNA Precursor of Tetrahymena: Involvement of a Guanosine Nucleotide in the Excision of the Intervening Sequence," *Cell* 27:487-496 (1981).

Kruger et al., "Self-Splicing RNA: Autoexcision and Autocyclization of the Ribosomal RNA Intervening Sequence of Tetrahymena," *Cell* 31:147-157 (1982).

Rossi, "Controlled, targeted, intracellular expression of ribozymes: progress and problems," *TIBTECH* 13:301-306 (1995).

Been and Cech, "One Binding Site Determines Sequence Specificity of Tetrahymena Pre-rRNA Self-Splicing, Trans-Splicing, Trans-Splicing and RNA Enzyme Activity," *Cell* 47:207-216 (1986).

Cech, "Ribozyme Engineering," *Current Opinion in Structural Biology* 2:605-609 (1992).

Dzierzak et al., "Lineage-specific Expression of a Human β-globin Gene in Murine Bone Marrow Transplant Recipients Reconstituted with Retrovirus-Transduced Stem Cells," *Nature* 331:35-41 (1989).

Konarska et al., "*Trans* Splicing of mRNA Precursors in Vitro," *Cell* 42:165-171 (1985).

Kruger et al., "Self-Splicing RNA: Autoexcision and Autocyclization of the Ribosomal RNA Intervening Sequence of Tetrahymena," *Cell* 31:147-157 (1982),.

Malim et al., "Functional Dissection of the HIV-1 Rev *Trans*-Activator—Derivation of a *Trans*-Dominant Repressor of Rev Function" *Cell* 58:205-214 (1989).

Morgan and Anderson, "Human Gene Therapy," *Annu. Rev. Biochem.* 62:191-217 (1993).

Murphy and Cech, "Alteration of Substrate Specificity for the Endoribonucleolytic Cleavage of RNA by the *Tetrahymena* Ribozyme," *Proc. Natl. Acad. Sci. USA* 86:9218-9222 (1989).

Price and Cech, "Coupling of *Tetrahymena* Ribosomal RNA Splicing to β-Galactosidase Expression in *Escherichia coli*," *Science* 228:719-722 (1985).

Price and Cech, "Determinants of the 3' Splice Site for Self-splicing of the *Tetrahymena* pre-rRNA," *Genes & Development* 2:1439-1447 (1988).

Sarver et al., "Ribozymes as Potential Anti-HIV-1 Therapeutic Agents" *Science* 247:1222-1225 (1990).

Smith et al., "Development of a *lacZ* Marked WEHI-3B D$^+$Murine Leukemic Cell Line as an *In-Vivo* Model of Acute Non-Lymphocytic Leukemia," *Leukemia* 7:310-317 (1993).

Solnick, "*Trans* Splicing on mRNA Precursors," *Cell* 42:157-164 (1985).

Sullenger et al., "Overexpression of TAR Sequences Renders Cells Resistant to Human Immunodeficiency Virus Replication," *Cell* 63:601-608 (1990).

Trono et al., "HIV-1 Gag Mutants Can Dominantly Interfere with the Replication of the Wild-type Virus," *Cell* 59:113-120 (1989).

Tsuchihashi et al., "Protein Enhancement of Hammerhead Ribozyme Catalysis," *Science* 262:99-102 (1993).

van der Veen et al., "Excised Group II Introns in Yeast Mitochondria are Lariats and Can Be Formed by Self-splicing In Vitro," *Cell* 44:225-234 (1986).

Waring et al., "The Tetrahymena rRNA Intron Self-Splices in E. Coli: In Vivo Evidence for the Importance of Key Base-Paired Regions of RNA for RNA Enzyme Function," *Cell* 40:371-380 (1985).

Weber et al., "Antiviral properties of a dominant negative mutant of the herpes simplex virus type 1 regulatory protein ICP0," *Journal of General Virology* 73:2955-2961 (1992).

Zaug and Cech, "The Intervening Sequence RNA of *Tetrahymena* Is a Enzyme," *Science* 231:470-475 (1986).

Zaug et al., "The *Tetrahymena* Ribozyme Acts Like an RNA Restriction Endonuclease," *Nature* 324:429-433 (1986).

* cited by examiner

Figure 1: Targeted Trans-Splicing
A. Self-Splicing of the Group I Intron from *Tetrahymena thermophila* pre-rRNA
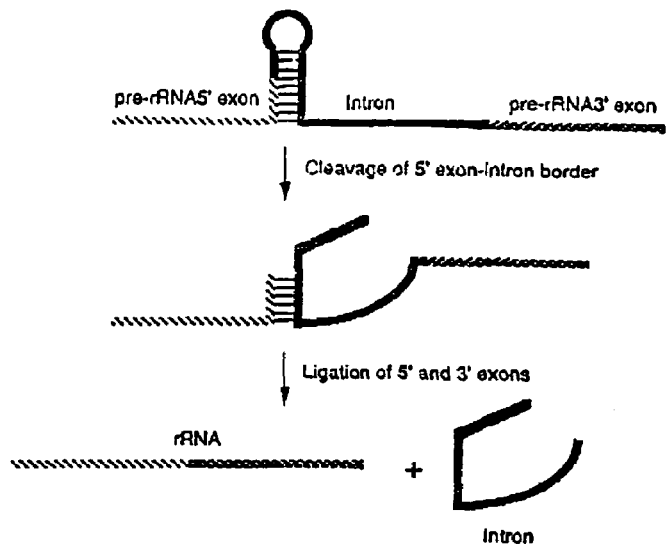
B. Trans-splicing of a 3' exon onto a dinucleotide 5' exon
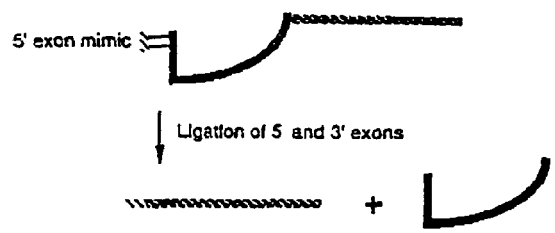
C. Targeted trans-splicing of a new 3' exon onto a targeted 5' exon
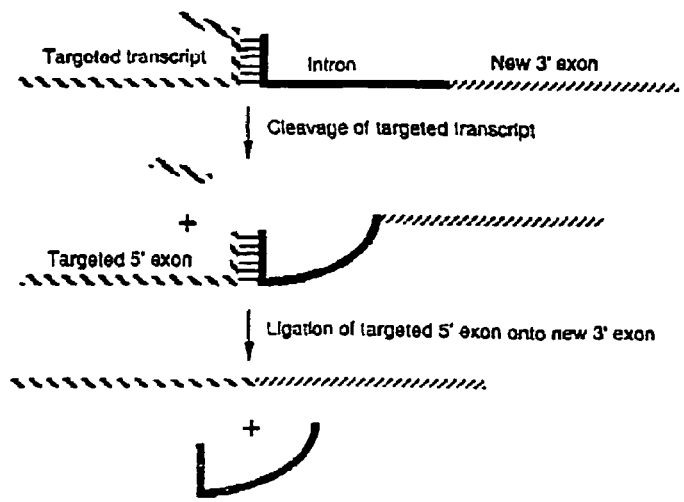

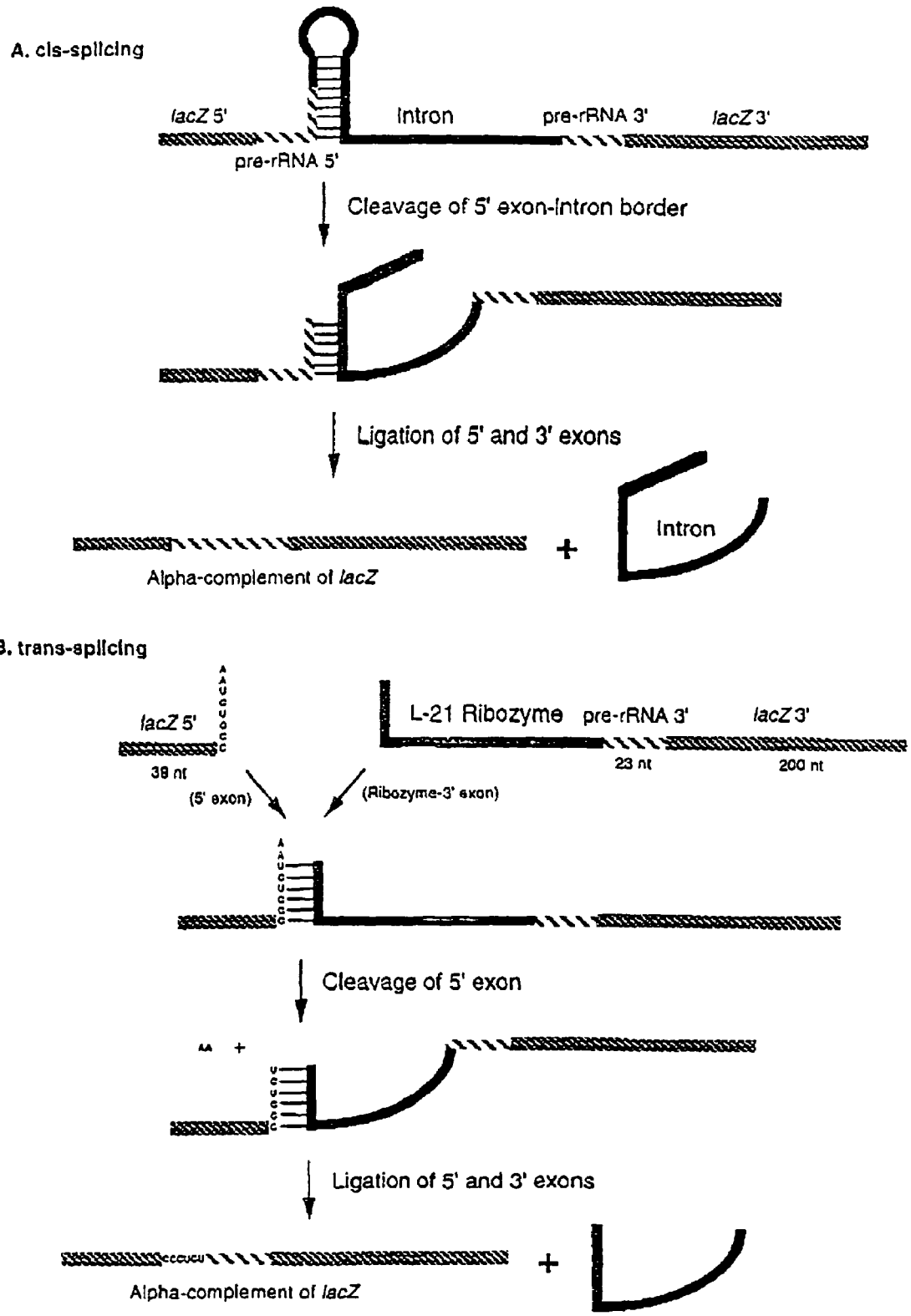
Figure 2: cis- and trans-splicing to recreate lacZ (alpha complement) transctipts

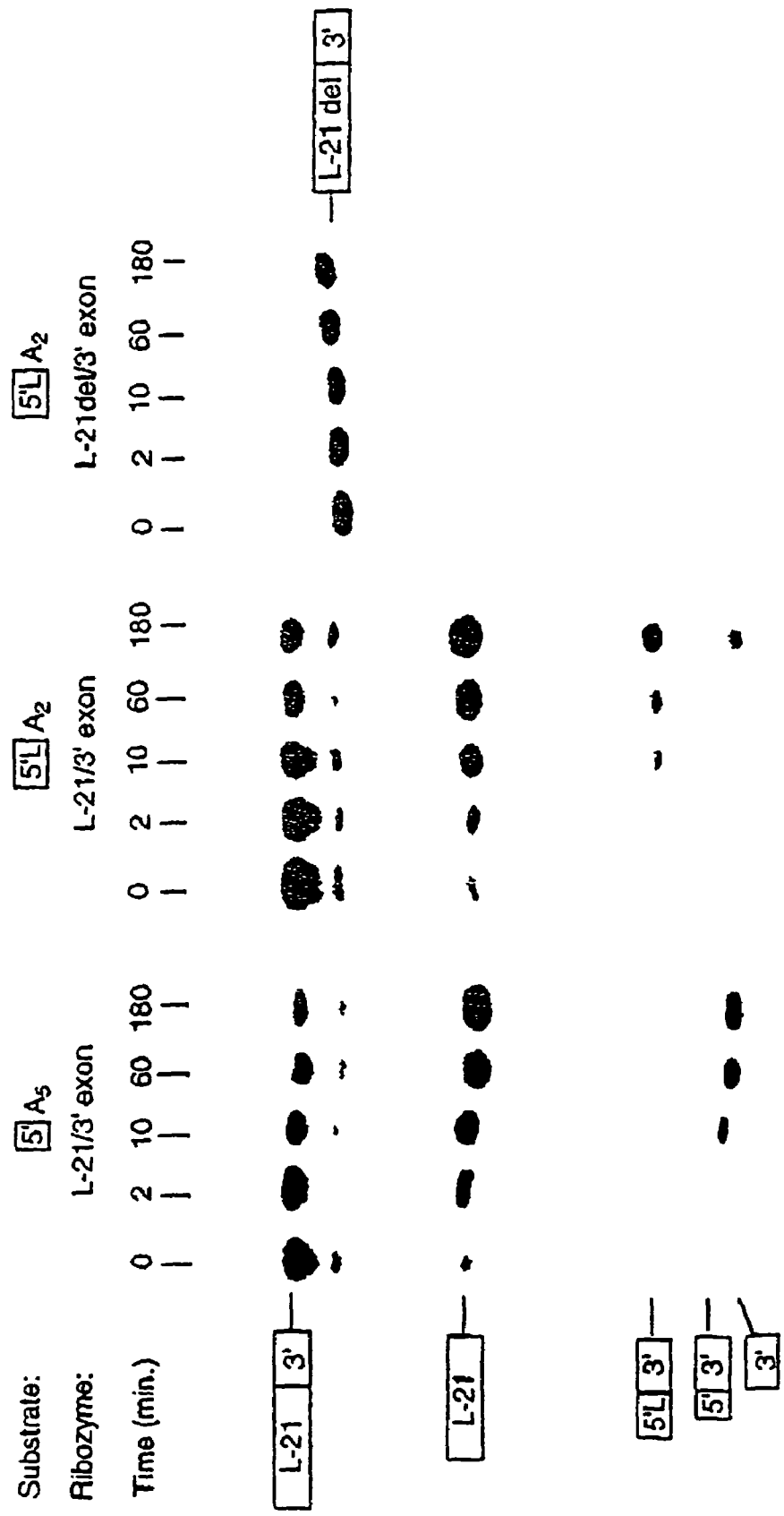

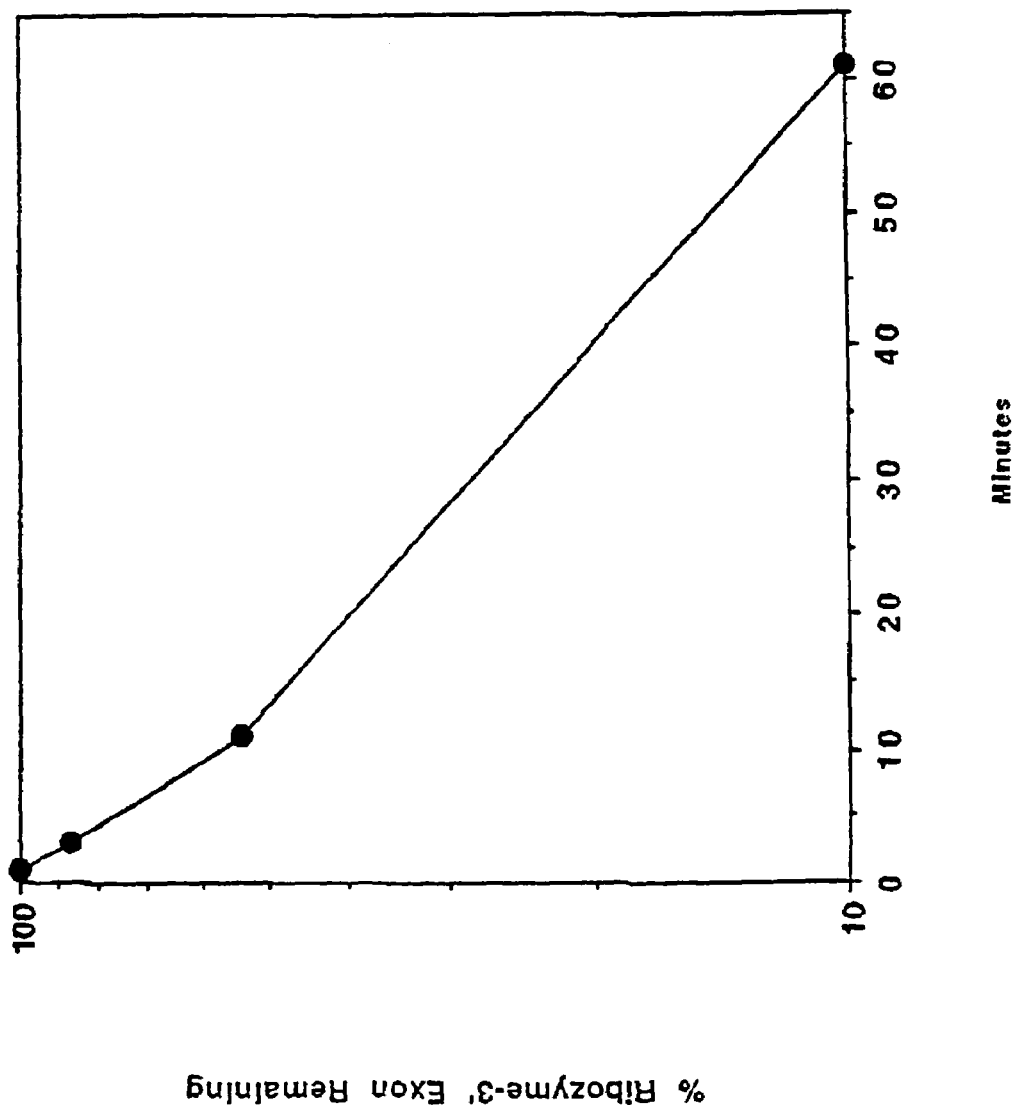

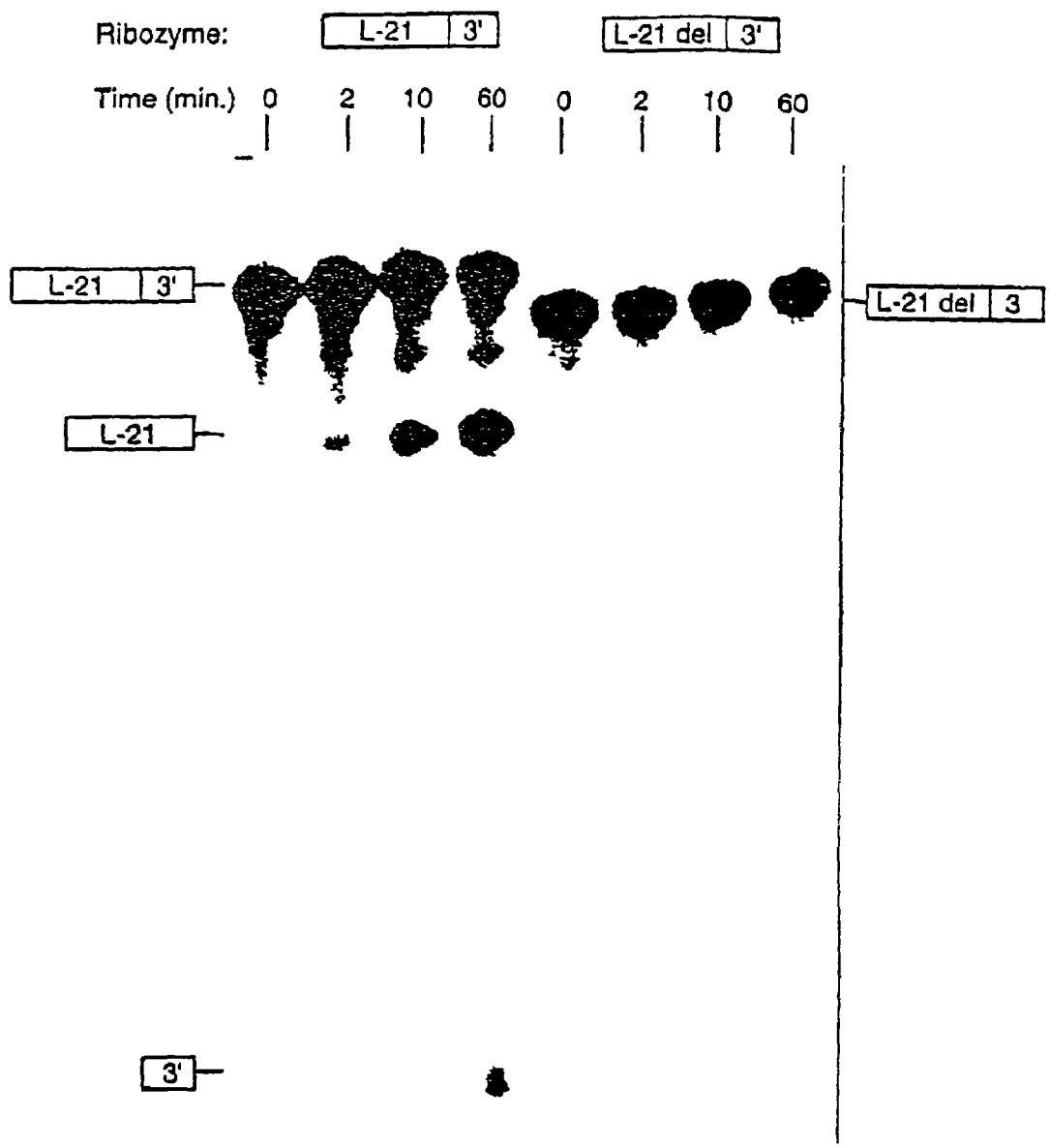
Figure 5: Hydrolysis releases the 200 nucleotide *lacZ* 3' Exon Sequence Figure 6: Trans-Splicing to Correct a 1106 Nucleotide Truncated *lacZ* Transcript
A. Trans-splicing scheme
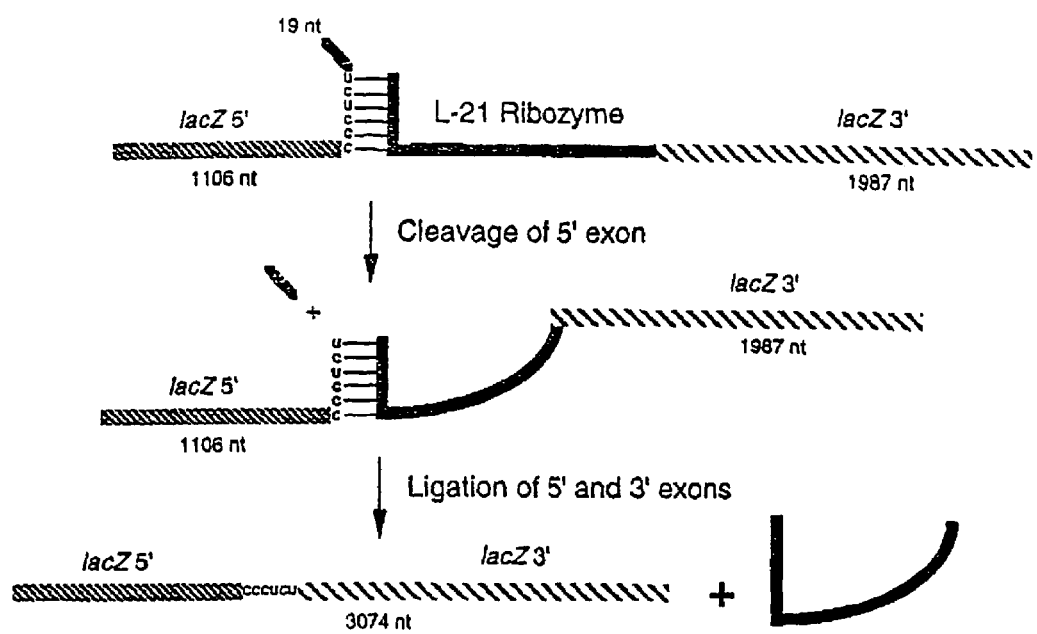
B. Trans-splicing reaction
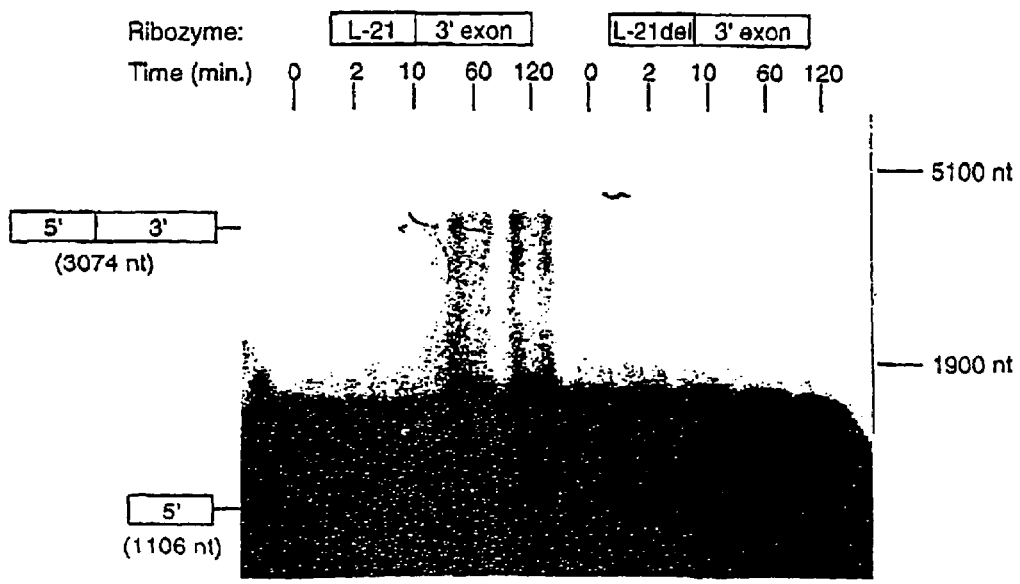

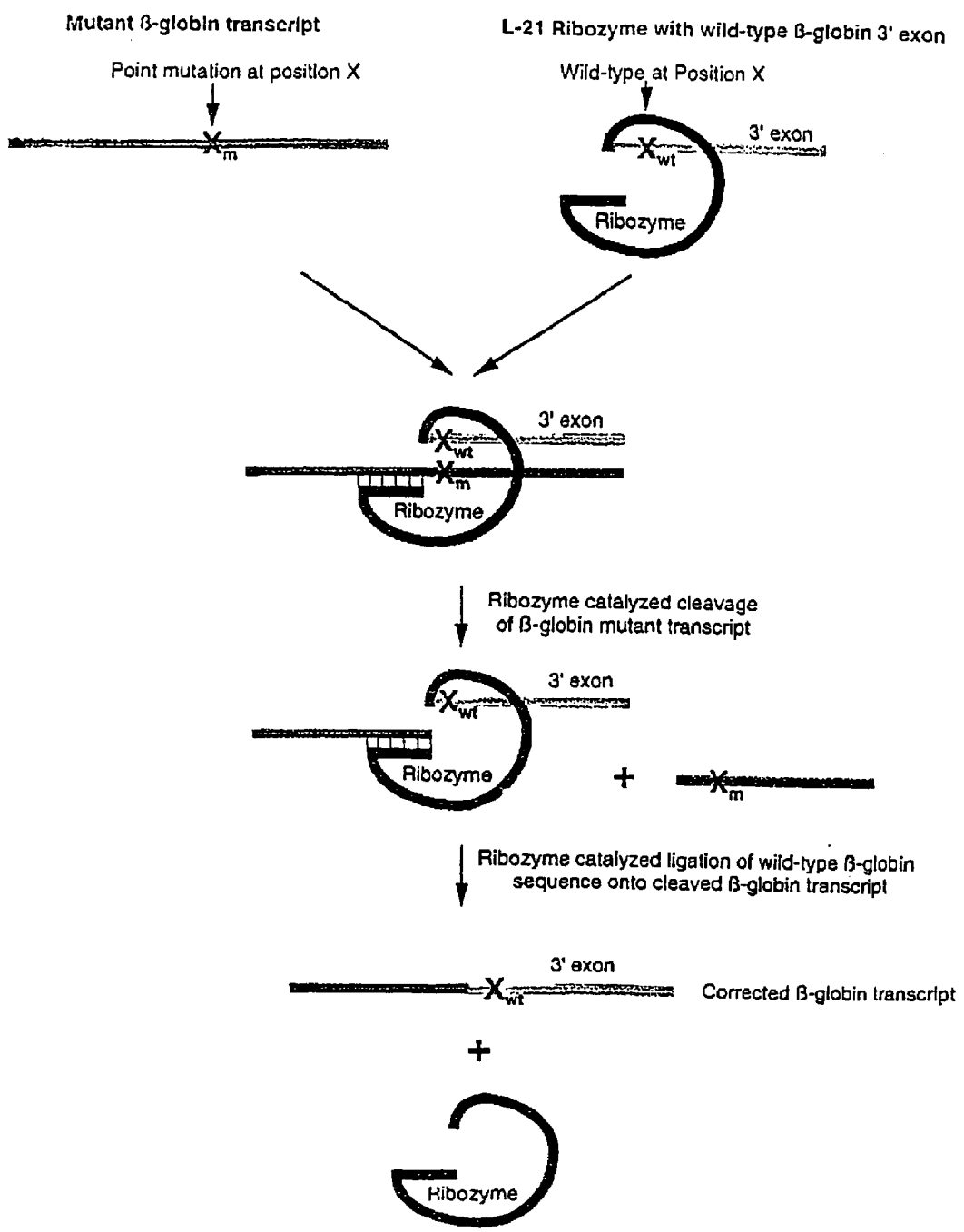
Figure 7: Targeted Trans-Splicing to Correct Mutant β-globin Transcripts

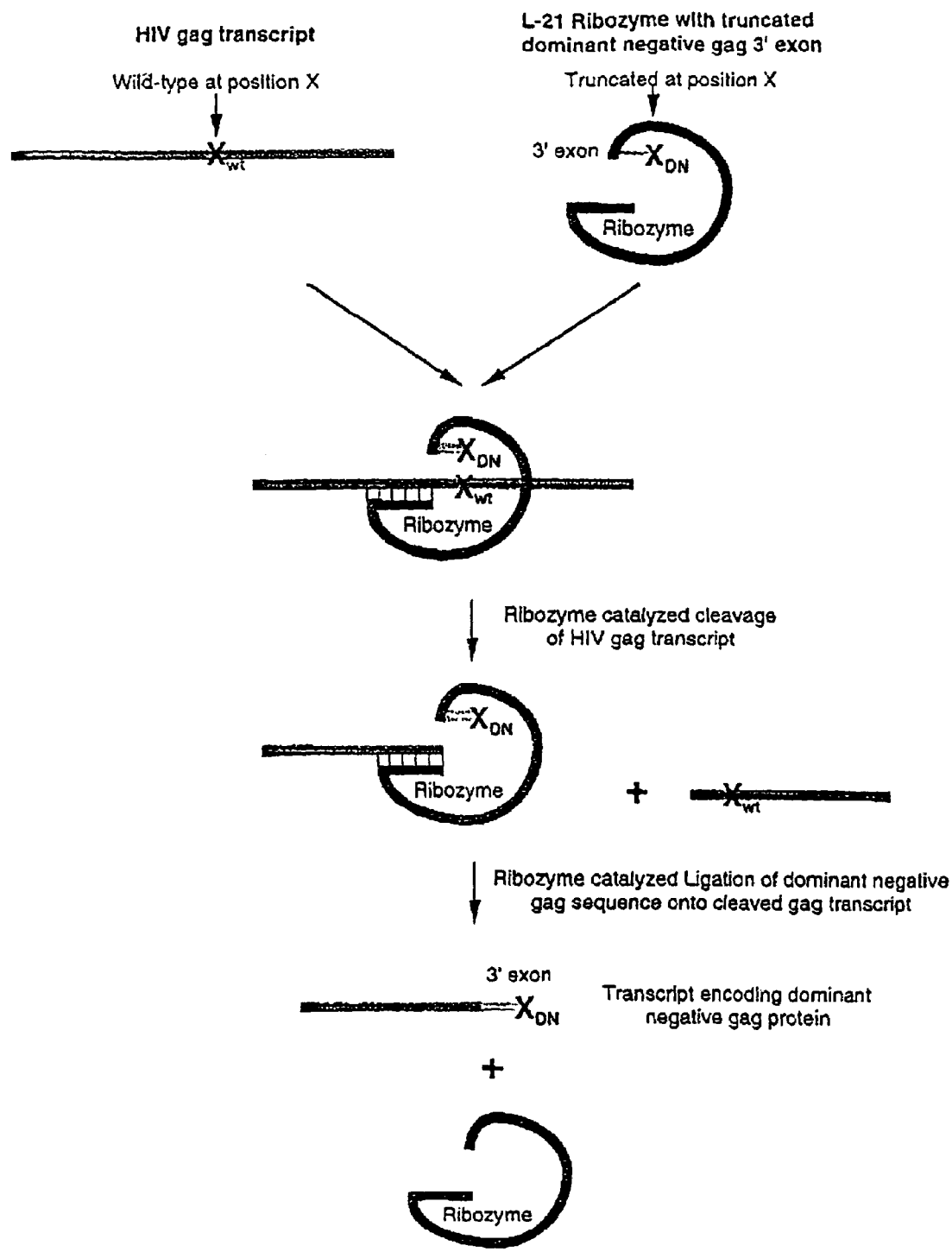
Figure 8: Targeted Trans-Splicing to Mutate HIV gag Encoding Transcripts

ALTERATION OF SEQUENCE OF A TARGET MOLECULE

This is a continuation of Application Ser. No. 09/165,514 filed Oct. 2, 1998, U.S. Pat. No. 6,897,016 which is a continuation of Application Ser. No. 08/786,753 filed Jan. 24, 1997, U.S. Pat. No. 5,869,254, which is a continuation of Application Ser. No. 08/152,450 filed Nov. 12, 1993, U.S. Pat. No. 5,667,969.

This invention relates to therapy of diseases using ribozymes.

The following is a brief history of the discovery and activity of enzymatic RNA molecules or ribozymes. This history is not meant to be complete but is provided only for understanding of the invention that follows. This summary is not an admission that all of the work described below is prior art to the claimed invention.

Prior to the 1970s it was thought that all genes were direct linear representations of the proteins that they encoded. This simplistic view implied that all genes were like ticker tape messages, with each triplet of DNA "letters" representing one protein "word" in the translation. Protein synthesis occurred by first transcribing a gene from DNA into RNA (letter for letter) and then translating the RNA into protein (three letters at a time). In the mid 1970s it was discovered that some genes were not exact, linear representations of the proteins that they encode. These genes were found to contain interruptions in the coding sequence which were removed from, or "spliced out" of, the RNA before it became translated into protein. These interruptions in the coding sequence were given the name of intervening sequences (or introns) and the process of removing them from the RNA was termed splicing. A general reference for spliceosomes and how they are related to self-splicing introns is Guthrie, C., 253 *Science* 157, 1991. After the discovery of introns, two questions immediately arose: (i) why are introns present in genes in the first place, and (ii) how do they get removed from the RNA prior to protein synthesis? The first question is still being debated, with no clear answer yet available. The second question, how introns get removed from the RNA, is much better understood after a decade and a half of intense research on this question. At least three different mechanisms have been discovered for removing introns from RNA. Two of these splicing mechanisms involve the binding of multiple protein factors which then act to correctly cut and join the RNA. A third mechanism involves cutting and joining of the RNA by the intron itself, in what was the first discovery of catalytic RNA molecules.

Cech and colleagues were trying to understand how RNA splicing was accomplished in a single-celled pond organism called *Tetrahymena thermophila*. They had chosen *Tetrahymena thermophila* as a matter of convenience, since each individual cell contains over 10,000 copies of one intron-containing gene (the gene for ribosomal RNA). They reasoned that such a large number of intron-containing RNA molecules would require a large amount of (protein) splicing factors to get the introns removed quickly. Their goal was to purify these hypothesized splicing factors and to demonstrate that the purified factors could splice the intron-containing RNA in vitro. Cech rapidly succeeded in getting RNA splicing to work in vitro, but something funny was going on. As expected, splicing occurred when the intron-containing RNA was mixed with protein-containing extracts from *Tetrahymena*, but splicing also occurred when the protein extracts were left out. Cech proved that the intervening sequence RNA was acting as its own splicing factor to snip itself out of the surrounding RNA. They published this startling discovery in 1982. Continuing studies in the early 1980's served to elucidate the complicated structure of the *Tetrahymena* intron and to decipher the mechanism by which self-splicing occurs. Many research groups helped to demonstrate that the specific folding of the *Tetrahymena* intron is critical for bringing together the parts of the RNA that will be cut and spliced. Even after splicing is complete, the released intron maintains its catalytic structure. As a consequence, the released intron is capable of carrying out additional cleavage and splicing reactions on itself (to form intron circles). By 1986, Cech was able to show that a shortened form of the *Tetrahymena* intron could carry out a variety of cutting and joining reactions on other pieces of RNA. The demonstration proved that the *Tetrahymena* intron can act as a true enzyme: (i) each intron molecule was able to cut many substrate molecules while the intron molecule remained unchanged, and (ii) reactions were specific for RNA molecules that contained a unique sequence (CUCU) which allowed the intron to recognize and bind the RNA. Zaug and Cech coined the term "ribozyme" to describe any ribonucleic acid molecule that has enzyme-like properties. Also in 1986, Cech showed that the RNA substrate sequence recognized by the *Tetrahymena* ribozyme could be changed by altering a sequence within the ribozyme itself. This property has led to the development of a number of site-specific ribozymes that have been individually designed to cleave at other RNA sequences. The *Tetrahymena* intron is the most well-studied of what is now recognized as a large class of introns, Group I introns. The overall folded structure, including several sequence elements, is conserved among the Group I introns, as is the general mechanism of splicing. Like the *Tetrahymena* intron, some members of this class are catalytic, i.e., the intron itself is capable of the self-splicing reaction. Other Group I introns require additional (protein) factors, presumably to help the intron fold into and/or maintain its active structure. While the *Tetrahymena* intron is relatively large, (413 nucleotides) a shortened form of at least one other catalytic intron (SunY intron of phage T4, 180 nucleotides) may prove advantageous not only because of its smaller size but because it undergoes self-splicing at an even faster rate than the *Tetrahymena* intron.

Ribonuclease P (RNAseP) is an enzyme comprised of both RNA and protein components which are responsible for converting precursor tRNA molecules into their final form by trimming extra RNA off one of their ends. RNAseP activity has been found in all organisms tested, but the bacterial enzymes have been the most studied. The function of RNAseP has been studied since the mid-1970s by many labs. In the late 1970s, Sidney Altman and his colleagues showed that the RNA component of RNAseP is essential for its processing activity; however, they also showed that the protein component also was required for processing under their experimental conditions. After Cech's discovery of self-splicing by the *Tetrahymena* intron, the requirement for both protein and RNA components in RNAseP was reexamined. In 1983, Altman and Pace showed that the RNA was the enzymatic component of the RNAseP complex. This demonstrated that an RNA molecule was capable of acting as a true enzyme, processing numerous tRNA molecules without itself undergoing any change. The folded structure of RNAseP RNA has been determined, and while the sequence is not strictly conserved between RNAs from different organisms, this higher order structure is. It is thought that the protein component of the RNAseP complex may serve to stabilize the folded RNA in vivo. At least one RNA position important both to substrate recognition and to determination of the cleavage site has been identified, however little else is known about the active site. Because tRNA sequence recognition is minimal, it is clear that some aspect(s) of the tRNA structure must also be involved in substrate recognition and cleavage activity. The size of RNAseP RNA (>350 nucleotides), and the complexity of the substrate recognition, may limit the potential for the use of an RNAseP-like RNA in therapeutics. However, the size of RNAseP is being trimmed down (a molecule of only 290 nucleotides functions reasonably well). In addition, substrate recognition has been simplified by the recent discovery that RNAseP RNA can cleave small RNAs lacking the natural tRNA secondary structure if an additional RNA (containing a "guide" sequence and a sequence element naturally present at the end of all tRNAs) is present as well.

Symons and colleagues identified two examples of a self-cleaving RNA that differed from other forms of catalytic RNA already reported. Symons was studying the propagation of the avocado sunblotch viroid (ASV), an RNA virus that infects avocado plants. Symons demonstrated that as little as 55 nucleotides of the ASV RNA was capable of folding in such a way as to cut itself into two pieces. It is thought that in vivo self-cleavage of these RNAs is responsible for cutting the RNA into single genome-length pieces during viral propagation. Symons discovered that variations on the minimal catalytic sequence from ASV could be found in a number of other plant pathogenic RNAs as well. Comparison of these sequences revealed a common structural design consisting of three stems and loops connected by central loop containing many conserved (invariant from one RNA to the next) nucleotides. The predicted secondary structure for this catalytic RNA reminded the researchers of the head of a hammer; thus it was named as such. Uhlenbeck was successful in separating the catalytic region of the ribozyme from that of the substrate. Thus, it became possible to assemble a hammerhead ribozyme from 2 (or 3) small synthetic RNAs. A 19-nucleotide catalytic region and a 24-nucleotide substrate were sufficient to support specific cleavage. The catalytic domain of numerous hammerhead ribozymes have now been studied by both the Uhlenbeck and Symons groups with regard to defining the nucleotides required for specific assembly and catalytic activity and determining the rates of cleavage under various conditions.

Haseloff and Gerlach showed it was possible to divide the domains of the hammerhead ribozyme in a different manner. By doing so, they placed most of the required sequences in the strand that didn't get cut (the ribozyme) and only a required UH where H=C, A, or U in the strand that did get cut (the substrate). This resulted in a catalytic ribozyme that could be designed to cleave any UH RNA sequence embedded within a longer "substrate recognition" sequence. The specific cleavage of a long mRNA, in a predictable manner using several such hammerhead ribozymes, was reported in 1988.

One plant pathogen RNA (from the negative strand of the tobacco ringspot virus) undergoes self-cleavage but cannot be folded into the consensus hammerhead structure described above. Bruening and colleagues have independently identified a 50-nucleotide catalytic domain for this RNA. In 1990, Hampel and Tritz succeeded in dividing the catalytic domain into two parts that could act as substrate and ribozyme in a multiple-turnover, cutting reaction. As with the hammerhead ribozyme, the hairpin catalytic portion contains most of the sequences required for catalytic activity while only a short sequence (GUC in this case) is required in the target. Hampel and Tritz described the folded structure of this RNA as consisting of a single hairpin and coined the term "hairpin" ribozyme (Bruening and colleagues use the term "paper clip" for this ribozyme motif). Continuing experiments suggest an increasing number of similarities between the hairpin and hammerhead ribozymes in respect to both binding of target RNA and mechanism of cleavage. At the same time, the minimal size of the hairpin ribozyme is still 50–60% larger than the minimal hammerhead ribozyme.

Hepatitis Delta Virus (HDV) is a virus whose genome consists of single-stranded RNA. A small region (~80 nucleotides) in both the genomic RNA, and in the complementary anti-genomic RNA, is sufficient to support self-cleavage. As the most recently discovered ribozyme, HDV's ability to self-cleave has only been studied for a few years, but is interesting because of its connection to a human disease. In 1991, Been and Perrotta proposed a secondary structure for the HDV RNAs that is conserved between the genomic and anti-genomic RNAs and is necessary for catalytic activity. Separation of the HDV RNA into "ribozyme" and "substrate" portions has recently, been achieved by Been, but the rules for targeting different substrate RNAs have not yet been determined fully. Been has also succeeded in reducing the size of the HDV ribozyme to ~60 nucleotides.

The table below lists some of the characteristics of the ribozymes discussed above:

TABLE 1

Characteristics of ribozymes

Group I Introns

Size: ~300 to >1000 nucleotides.
Requires a U in the target sequence immediately 5' of the cleavage site.
Binds 4–6 nucleotides at 5' side of cleavage site.
Over 75 known members of this class. Found in Tetrahymena thermophila rRNA, fungal mitochondria, chloroplasts, phage T4, blue-green algae, and others.

RNAseP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.

Hammerhead Ribozyme

Size: ~30 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent.

Hairpin Ribozyme

Size: ~50 nucleotides.
Requires the target sequence GUC immediately 3' of the cleavage site.
Binds 4 nucleotides at 5' side of the cleavage site and a variable number to the 3' side of the cleavage site.
Only 1 known member of this class. Found in one plant pathogen (satellite RNA of the tobacco ringspot virus) which uses RNA as the infectious agent.

Hepatitis Delta Virus (HDV) Ribozyme

Size: ~60 nucleotides (at present).
Cleavage of target RNAs recently demonstrated.
Sequence requirements not fully determined.
Binding sites and structural requirements not fully determined, although no sequences 5' of cleavage site are required.
Only 1 known member of this class. Found in human HDV.

As the term is used in this application, ribozymes are RNA molecules having an enzymatic activity which is able to cleave and splice other separate RNA molecules in a nucleotide base sequence specific manner. Such enzymatic RNA molecules can be targeted to virtually any RNA transcript, and efficient cleavage and splicing achieved in vitro. Kim et al., 84 *Proc. Nat. Acad. of Sci. USA* 8788, 1987, Hazeloff et al., 234 *Nature* 585, 1988, Cech, 260 *JAMA* 3030, 1988, and Jefferies et al., 17 *Nucleic Acid Research* 1371, 1989.

Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts to cut and splice the target RNA. Strategic cleavage and splicing of such a target RNA will destroy its ability to direct synthesis of an encoded protein. After a ribozyme has bound, cleaved and spliced its RNA target it is released from that RNA.

By the phrase "catalytic" or "enzymatic RNA molecule" is meant an RNA molecule which has complementarity in a substrate binding region to a specified gene target, and also has an enzymatic activity which is active to specifically cleave and splice RNA in that target. That is, the enzymatic RNA molecule is able to intermolecularly cleave and splice RNA and thereby alter a target RNA molecule. This complementarity functions to allow sufficient hybridization of the enzymatic RNA molecule to the target RNA to allow the cleavage to occur. 100% complementarity is preferred, but complementarity as low as 50–75% may also be useful in this invention.

In preferred embodiments of this invention, the enzymatic RNA molecule is formed in a hammerhead motif, but may also be formed in the motif of a hairpin, hepatitis delta virus, group I intron or RNAseP RNA (in association with an RNA guide sequence). Examples of such hammerhead motifs are described by Rossi et al., 8 AIDS RESEARCH AND HUMAN RETROVIRUSES 183, 1992, of hairpin motifs by Hampel et al., RNA CATALYST FOR CLEAVING SPECIFIC RNA SEQUENCES, filed Sep. 20, 1989, which is a continuation-in-part of U.S. Ser. No. 07/247,100 filed Sep. 20, 1988, Hampel and Tritz, 28 *Biochemistry* 4929, 1989 and Hampel et al., 18 *Nucleic Acids Research* 299, 1990, and an example of the hepatitis delta virus motif is described by Perrotta and Been, 31 *Biochemistry* 16, 1992, of the RNAseP motif by Guerrier-Takada et al., 35 *Cell* 849, 1983, and of the group I intron by Cech et al., U.S. Pat. No. 4,987,071. These specific motifs are not limiting in the invention and those skilled in the art will recognize that all that is important in an enzymatic RNA molecule of this invention is that it has a specific substrate binding site which is complementary to one or more of the target gene RNA regions, and that it have nucleotide sequences within or surrounding that substrate binding site which impart an RNA cleaving activity to the molecule.

The invention provides a method for designing a class of enzymatic cleaving and splicing agents which exhibit a high degree of specificity for the RNA of a desired target. The ribozyme molecule is preferably targeted to a highly conserved sequence region of a target such that specific treatment of a disease or condition can be provided with a single ribozyme. Such enzymatic RNA molecules can be delivered exogenously to specific cells as required.

Synthesis of ribozymes greater than 100 nucleotides in length is very difficult using automated methods, and the therapeutic cost of such molecules is prohibitive. However, delivery of such ribozymes by expression vectors is primarily feasible using ex vivo treatments.

Inoue et al., 43 *Cell* 431, 1985, state that short oligonucleotides of 2–6 nucleotides can undergo intermolecular exon ligation or splicing in trans. It indicates that "long 5' exons should be reactive provided that three conditions are met: the exon must have a 3' hydroxyl group, it must terminate in a sequence similar to that of the 3' end of the 5' exon, and the 3' terminal sequence must be available as opposed to being tied up in some secondary structure. Thus, it appears that exon switching is possible in this system, though limited by the availability of alternative 5' exons that meet the above criteria. These could include transcripts that are not 5' exons from other precursors, since RNA polymerases always leave 3' hydroxyl ends".

SUMMARY OF THE INVENTION

This invention features a method in which natural transcripts are altered by use of a splicing reaction in vivo or in vitro. It involves the manipulation of genetic information to ensure that a useful transcript is provided within a cellular system or extract.

In a first aspect, the invention features a method for splicing a target nucleic acid molecule with a separate nucleic acid molecule. Such splicing generally causes production of a chimeric protein with advantageous features over that protein naturally produced from the target nucleic acid prior to splicing. The method includes contacting the target nucleic acid molecule with a catalytic nucleic acid molecule including the separate nucleic acid molecule. Such contacting is performed under conditions in which at least a portion of the separate nucleic acid molecule is spliced with at least a portion of the target nucleic acid molecule to form a chimeric nucleic acid molecule. In this method, the catalytic nucleic acid molecule is chosen so that it is not naturally associated with the separate nucleic acid molecule.

The target nucleic acid molecule can be any desired molecule with which a splicing reaction can occur. Generally, this will be an RNA molecule, preferably a messenger RNA molecule, but it may also include molecules that have one or more non-ribonucleotides substituents, such as deoxyribonucleotides or other analogs as described by Usman et al., PCT/US93/00833 and Eckstein et al. EP90/01731, both hereby incorporated by reference.

Generally, the target nucleic acid molecule is present within a cell and is chosen or targeted because it encodes a defective protein or is deleterious to that cell. Splicing of the separate nucleic acid molecule with such a target nucleic molecule is designed to alter the protein product of that nucleic acid molecule. Such alteration causes production of a useful protein which will allow that cell to either survive or die, as desired. Thus, for example, in a gene therapy setting, the target nucleic acid molecule may encode a non-functional protein necessary for normal life. This molecule can be spliced with a separate nucleic acid molecule to allow appropriate expression of a functional protein. Alternatively, the splicing may cause production of a more stable protein, or of a protein which acts as an agonist or antagonist of a function, e.g., a viral or bacterial replication function.

The separate nucleic acid molecule is generally chosen such that it encodes a 3' exon which it is desirable to express within a cell. This exon will generally not include control sequences such as promoter regions, but may include poly (A) tails and other stabilizing or enhancing functions well known in the art. As with the target nucleic acid molecule, the separate nucleic acid molecule generally is a ribonucleic acid molecule but may be substituted as described above.

By "enzymatic" or "catalytic nucleic acid molecule" is meant a molecule having a motif generally as described above in the Background of the Invention, which and is preferably selected from the motif of a group I or group II intron having a cleavage and splicing activity. Alternatively, the splicing or cleavage activity may be provided by a different nucleic acid molecule, or may supplement the catalytic nucleic acid molecule. Those of ordinary skill in the art will recognize that other motifs than those of the group I and group II introns may also be manipulated to provide useful splicing activity.

The conditions chosen for the contacting step may be those naturally occurring within a cell, or may be manipulated in vitro to ensure that the splicing reaction will occur. These conditions are well known to those in the art, for example, as described by Inoue et al., supra.

By at least a portion of the respective nucleic acid molecules is meant that the 5' end of the target nucleic acid molecule will be spliced with the 3' end of the separate nucleic acid molecule. Such a portion may be only a few nucleotides (10–500 nucleotides) or may be significantly greater and may represent almost all of a molecule encoding a gene product (i.e., at least 1 to 5 kbases).

The chimeric nucleic acid molecule is one which may occur naturally in nature but is not present prior to the splicing reaction. Alternatively, it may be a completely novel structure which does not occur in nature, but which is useful in gene therapeutic treatment of an organism.

The catalytic nucleic acid molecule is not naturally associated with the separate nucleic acid molecule since it is not generally desired to splice the 3' end of a naturally occurring catalytic nucleic acid molecule with a target nucleic acid molecule. Rather, the separate nucleic acid molecule is chosen or selected to have a beneficial function once spliced with the target nucleic molecule.

In a related aspect, the invention features a method for splicing a target nucleic acid molecule with a separate nucleic acid molecule by contacting those molecules in the presence of one or more splicing factors or spliceosomes under splicing conditions. Such molecules are not naturally spliced together in nature, although the final splice product may be a natural product.

The various splicing factors and spliceosomes are well known in the art, and this activity is generally described by Bruzik and Maniatis in 360 *Nature* 692, 1992, hereby incorporated by reference herein. The invention concerns splicing of target nucleic acid molecules and separate nucleic acid molecules which are not normally spliced together within a cell as described by Bruzik and Maniatis, supra. Rather, as described above, a separate nucleic acid molecule is selected such that a useful function can be achieved in a gene therapeutic fashion.

In preferred embodiments, the catalytic nucleic acid is able to cleave and splice, e.g., it has a group I or group II intron motif; the method is performed in vitro or in vivo with an RNA target; and the method can be used to treat genetic disease in a gene therapy type manner, for example, by correcting an abnormal transcript, or by providing antiviral activity such as a dominant negative allele to a viral RNA.

In other aspects, the invention features catalytic nucleic acid molecules having a selected separate nucleic acid molecule as a 3' exon encoding at least a portion of a useful gene which can be used in gene therapy. Such a molecule can be spliced with and thereby correct or modify the expression of other target RNA molecules. The invention also features vectors encoding such catalytic nucleic acid molecules.

The observation that ribozymes can specifically cleave targeted RNAs in vitro has led to much speculation about their potential usefulness as gene inhibitors. By cleaving targeted mRNAs in vivo, ribozymes can be used to stop the flow of genetic information. Here we describe a different application of ribozymes. For example, a group I intron ribozyme can be used to manipulate the flow of genetic information by targeted trans-splicing. Defective cellular transcripts may be repaired, or pathogen-derived transcripts may be altered to encode antagonists to the pathogen using such technology.

In nature the group I intron ribozyme from *Tetrahymena thermophila* self-splices itself from precursor ribosomal RNAs (T. R. Cech, A. J. Zaug, P. J. Grabowski, Cell 27 487 (1981); K. Kruger et al., Cell 31, 147 (1982)). This process is accomplished in two successive steps. First the phosphodiester bond at the 5' exon-intron border is cleaved. Then the 3' hydroxyl group on the 5' exon is covalently attached to the 3' exon, and the intron is removed (FIG. 1A). It has been previously demonstrated in vitro that the 5' exon in this reaction can be mimicked by RNA molecules supplied in trans; the minimum active unit is the dinucleotide substrate rCU (FIG. 1B) (T. Inoue, F. X. Sullivan, T. R. Cech, Cell 43, 431 (1985)). We propose use of trans-splicing reactions to ligate foreign sequences onto targeted transcripts after cleavage (FIG. 1C). In this manner, ribozymes can be employed to manipulate the flow of genetic information inside cells by changing what a targeted RNA encodes.

Other features and advantages of the invention will be apparent from the following description of the preferred embodiments thereof, and from the claims.

DESCRIPTION OF THE PREFERRED EMBODIMENTS

The drawings will briefly be described.

Drawings

FIGS. 1A, 1B, and 1C are diagrammatic representations showing reactions of the group I intron from *Tetrahymena* for targeted trans-splicing.

FIGS. 2A and 2B are a comparison of cis- and trans-splicing reactions for LacZ transcripts.

FIG. 3 is a copy of an autoradiogram showing targeted trans-splicing to correct truncated transcripts from the alpha complement of LacZ 39 nucleotides long. L-21 (or L-21 del) ribozyme-3' exon chimeric RNAs (see FIG. 2B) ($^{32}$P-body-labeled) (200 nM) were preheated in reaction buffer [50 mM Hepes (pH 7.0), 150 mM NaCl, and 5 mM MgCl$_2$] at 50° C. for 5 minutes and then equilibrated at 37° C. for 2 minutes. The 13 (5'-A$_5$: GGCCCUCUA$_5$) or 39 (5'L-A$_2$: see FIG. 2B) nucleotide substrate RNAs (1 µM) and GTP (100 µM) were preheated to 37° C. and added to the ribozymes to start the reactions which proceeded at 37° C. Portions containing one fifteenth of the reactions were removed at 0, 2, 10, 60, and 180 minutes and added to an equal volume of 10 mM EDTA to stop the reactions. Reaction products were analyzed upon a 4% polyacrylamide gel with 8M urea. The inactive L-21 del ribozyme was generated by deleting 93 nucleotide of the ribozyme (nucleotides 237–330 comprising L6b to P9).

FIG. 4 is a graphical representation of the targeted trans-splicing rate for correcting the 39 nucleotide truncated LacZ transcript. The products from the trans-splicing reaction time course containing the action L-21 ribozyme and the 39 nucleotide substrate shown in FIG. 2 were quantified with an AMBIS Image Acquisition and Analysis System (AMBIS, Inc., San Diego, Calif.). The percentage of the ribozyme-3' exon RNA remaining is plotted versus time.

FIG. 5 is a copy of an autoradiogram showing hydrolysis of the 3' LacZ exon attached to the L-21 ribozyme. L-21 (or L-21 del) ribozyme-3' exon chimeric RNAs ($^{32}$P-body-labeled) (100 nM) wee incubated at 37° C. in reaction buffer [50 mM-Hepes (pH 7.0), 150 mM NaCl, 5 mM MgCl$_2$, and 100 µM GTP]. A portion of the reaction was removed after 0, 2, 10, and 60 minutes and added to an equal volume of 10 mM EDTA to stop the reaction. Products were analyzed upon a 4% polyacrylamide gel containing 8M urea.

FIGS. 6A and 6B are representations of trans-splicing to recreate an entire 3074 nucleotide LacZ messenger RNA from a 1106 nucleotide truncated transcript. A. Scheme for correcting transcript. B. Trans-splicing reaction. L-21 (or L-21 del) ribozyme-3' exon chimeric RNAs (20 nM) were preheated in reaction buffer [50 mM Hepes (pH 7.0), 150 mM NaCl, and 5 mM MgCl$_2$] at 50° C. for 5 minutes and then equilibrated at 37° C. for 2 minutes. The 1106 nucleotide substrate RNA ($^{32}$P-end labeled) (200 nM) and GTP (100 µM) were preheated at 37° C. and added to the ribozymes to start the reactions which proceeded at 37° C. One sixth of each reaction was removed at 0, 2, 10, 60, and 180 minutes and added to an equal volume of 10 M EDTA to stop the reaction. Reaction products were analyzed upon a 1.2% agarose gel containing 1.1% formaldehyde. rRNAs from mouse NIH 3T3 cells were used to as 5100 and 1900 nt molecular weight markers. The remaining sixth of the reactions, which had proceeded for 120 minutes, were in vitro translated.

FIG. 7 is a scheme for correcting genetic mutations using targeted trans-splicing.

FIG. 8 is a scheme for mutating HIV transcripts using targeted trans-splicing.

TARGETED TRANS-SPLICING

The general scheme for a targeted trans-splicing is shown in FIG. 1 using the group I intron of *Tetrahymena thermophila* as an example. Those in the art will recognize that this example is not limiting in the invention and that other enzymatic RNA molecules having the appropriate splicing activity can be used in the invention. Alternatively, as discussed above, these molecules can be supplemented by other molecules having a suitable splicing activity, or by spliceosomes or splicing factors. Generally, the reaction involves base pairing of the catalytic nucleic acid molecule with the targeted transcript, cleavage of the targeted transcript, and then ligation of the 3' exon (separate nucleic acid molecule) with this targeted 5' exon. The catalytic nucleic acid is removed in the reaction. As will be noted, the specificity of the reaction can be changed by alteration of the substrate binding site in the catalytic nucleic acid molecule by methods well known in the art.

The following is an example of various constructs used to show the operability of the claimed invention. Those in the art will recognize that this example indicates the utility of the invention for both in vitro and in vivo splicing reactions. While significant utility will be attained in vivo by use of the present invention, those in the art will also recognize that in vitro utility is important and can be used to create chimeric transcripts for use in laboratory situations or in a clinical setting.

EXAMPLE 1

LacZ Fusion

To assess the feasibility of the targeted trans-splicing approach, we tested the ability of the *Tetrahymena* ribozyme to correct truncated LacZ transcripts with targeted trans-splicing. It has previously been shown that in *E. coli* the *Tetrahymena* self-splicing group I intron can efficiently splice itself from transcripts encoding the alpha-complement of β-galactosidase (β-gal) (FIG. 2A) (J. V. Price, T. R. Cech, Science 228, 719 (1985); Waring et al., Cell 40, 371 (1985)). Since this reaction proceeded very efficiently in cis, we decided to determine if the ribozyme could perform a similar reaction in trans.

This system consists of 2 RNA molecules (FIG. 2B): a ribozyme-3' exon RNA and a 5' exon RNA. The group I ribozyme used in this study lacks the first 21 nucleotides present in the full length intron from which it is derived (A. J. Zaug, T. R. Cech, Science 231, 470 (1986)). The first 23 nucleotides of the 3' exon are derived from the pre-rRNA 3' exon sequence from *Tetrahymena* (M. D. Been, T. R. Cech, Cell 47, 207 (1986)). This 23 nucleotide sequence is fused in-frame to 200 nucleotides of the alpha-complement of the LacZ gene (Been and Cech, supra). The 39 nucleotide 5' exon contains a ribosome binding site, the first 21 coding nucleotides of an alpha-complement LacZ transcript, the ribozyme recognition sequence CCCUCU, and two adenosines. These adenosines must be removed if trans-splicing is to correct these LacZ transcripts. (FIG. 2B). [Previous studies have shown that the sequence and length of the RNA following the CCCUCU is not critical for *Tetrahymena* ribozyme action (A. J. Zaug, M. D. Been, T. C. Cech, Nature 324, 429 (1986))].

In vitro, the ribozyme can quickly and accurately trans-splice this LacZ 3' exon onto the truncated 39 nucleotide LacZ 5' exon to generate an RNA product which encodes the alpha-complement of β-galactosidase (FIG. 3). The reaction proceeds with speed and efficiency similar to those seen in a reaction with a short 13 nucleotide substrate. The $t_{1/2}$ for the trans-splicing reaction with the 39 nucleotide substrate was determined to be 13 minutes under conditions of substrate excess (FIG. 4).

In these experiments, trans-splicing (production of 5'-3' or 5'L-3') occurred faster than hydrolysis (production of free 3' exon; see FIG. 2). The rate of hydrolysis of the 3' exon from the ribozyme was determined to be $t_{1/2}$—60 minutes in a separate experiment (FIG. 5). An inactive version of the L-21 ribozyme (L-21 del) was not able to perform either the trans-splicing or the hydrolysis reaction (FIGS. 3 and 5). Sequencing of the trans-splicing product confirmed that the ultimate and penultimate 3' adenosine nucleotide were correctly removed from the 5' exon-substrate RNA, and this cleaved 5' exon was accurately spliced onto the 3' exon (data not shown). The splice junction gave the proper reading frame for β-gal expression.

EXAMPLE 2 mRNA Splicing

To determine if targeted trans-splicing could be employed to correct mRNA-size RNA fragments, a transcript which contained the first 1106 nucleotides of the LacZ coding sequence as well as signals for in vitro translation was created and targeted for alteration by trans-splicing. The L-21 ribozyme was directed to cleave the truncated LacZ transcript 19 nucleotides from its 3' end and trans-splice a 3' exon brought in by the ribozyme onto the cleaved LacZ target RNA (FIG. 6A). The 3' exon sequence attached to the ribozyme encoded the last 1987 nucleotides of the LacZ coding sequence and no sequences from the *Tetrahymena* pre rRNA. Accurate trans-splicing of the 3' exon sequences onto the truncated transcript resulted in a 3074 nucleotide product which encoded the entire LacZ coding sequence (FIG. 6B).

Once again the inactive version of the ribozyme, (L-21 del) was unable to perform this reaction, confirming its expected dependence of the catalytic activity of the RNA itself. The trans-splicing products from the 120 minute time points of the reactions shown in FIG. 6 were in vitro translated in wheat germ extract, and the in vitro translated proteins were assayed for β-gal activity using a standard ONPG assay (C. Smith et al., Leukemia 7, 310 (1993)).

Proteins from trans-splicing reactions containing active ribozymes were shown to contain 1500 units [1000×OD420/(ml·min)] of β-gal activity, while no activity was found in proteins translated from reactions containing the inactive ribozyme. Therefore, trans-splicing can be employed to correct the coding sequence of large defective transcripts.

In the reaction shown in FIG. 6, the labeled substrate RNA is in a 10 fold excess to the ribozyme-3' exon RNA. Therefore, only 10% of the labeled substrate RNAs could at best be converted to trans-spliced products. In this reaction however, we roughly estimate (by comparing different X-ray film exposures of the gel) that at most 1% of the truncated RNAs are corrected. This lack of efficiency is probably a result of the targeted RNAs adopting conformations which inhibit the ribozyme from correctly interacting with them. To improve the efficiency of this trans-splicing reaction, alternative sites for cleavage and splicing which are more accessible to the ribosome can be targeted by standard manipulation of this experiment. In vivo, cellular proteins may improve the efficiency of formation of the correct RNA interaction (Z. Tsuchihashi, M. Khosla, D. Herschlag, Science 262, 99 (1993)).

Uses

Gene mapping and human genome sequencing provides the genetic basis for an increasing number of inherited diseases. With each discovery or identification of a new disease-related gene there is an opportunity to develop gene therapy based treatments. Conventional gene therapy approaches attempt to correct a genetic deficiency by transferring a wild-type cDNA copy of a gene under the control of a heterologous promoter to cells harboring a defective copy of the gene. One obstacle for implementing such treatments is an inability to faithfully recapitulate the normal expression pattern of endogenous genes after gene transfer (R. A. Morgan, W. F. Anderson, Ann. Rev. Biochem. 62, 191 (1993); E. A. Dzierzak, T. Papayannopoulou, R. C. Mulligan, Nature 331, 35 (1989)). This may limit the number of genetic diseases treatable by gene therapy. Targeted trans-splicing offers a solution to this problem.

Ribozymes can be used to correct the defective transcripts issuing from mutant genes. This approach will be valuable for the treatment of the many genetic diseases caused by a common set of specific mutations which do not affect the expression of the mutant gene. For example, the genetic basis of many globin diseases is well understood. However, gene therapy based treatments for such diseases have been slow in coming, perhaps, because the expression patterns of the globin genes cannot be recapitulated after gene transfer. Targeted trans-splicing can potentially repair or correct globin transcripts that are either truncated or contain point mutations. In the process, the cellular expression pattern of these genes is maintained (FIG. 7). Therefore, targeted trans-splicing represents an important, novel strategy for the treatment of many genetic diseases.

Trans-splicing ribozymes based on any of the self-splicing group I introns can be designed to cleave a targeted transcript upstream of a specific mutation or upstream of a premature 3' end at essentially any uridine residue (F. L. Murphy, T. R. Cech, Proc. Natl. Acad. Sci, USA 86, 9218 (1989)). One simply changes the sequence of the internal guide sequence within the ribozyme (5'-GNNNNN) to match the sequence preceding the site of target RNA cleavage (5'-N'N'N'N'N'U), where N-N' represent any allowable base pair. The 3' exons attached to the ends of these ribozymes are comprised of a sequence designed to correct the mutant transcripts being targeted. The ribozyme will both cleave the mutant transcript and replace the mutant 3' region by a functional sequence. There is very little sequence requirement for a 3' exon in these reactions, so virtually any sequence can serve (J. V. Price, T. R. Cech, Genes and Development 2, 1439 (1988)). Thus, trans-splicing ribozymes can be made to correct essentially any mutant transcript because sequence requirements for 5' cleavage sites and 3' exons are minimal.

Trans-splicing ribozymes are also be effective antiviral agents. Several groups have employed trans-cleaving ribozymes to inhibit viral replication. Use of such ribozymes results in the destruction of the targeted viral RNA inside cells (N. Sarver et al., Science 247, 1222 (1990)). Thus, the effectiveness of these trans-cleavage ribozymes rests upon their ability to destroy the vast majority of the targeted viral RNAs. We propose employing trans-splicing ribozymes not to destroy viral RNAs, but to change the sequence of the viral RNAs to give them antiviral activity. For example, the HIV transcripts that encode the gag protein can be changed to encode a dominant negative version of this protein via targeted trans-splicing (FIG. 8) (M. H. Malim, E. Bohniein, J. Hauber, B. R. Culien, Cell 58, 205 (1989); D. Trono, M. B. Feinberg, D. Baltimore, Cell 59, 113 (1989)) or to contain a large number of TAR or RRE decoy RNAs (B. A. Sullenger, H. F. Gallardo, G. E. Ungers, E. Gilboa, Cell 63, 601 (1990)).

In contrast to trans-cleaving ribozymes, such antiviral trans-splicing ribozymes would have to affect only a small percentage of the targeted HIV transcripts to be effective at inhibiting viral replication. In general, the ability to change the information encoded by targeted transcripts by trans-splicing represents a broad new approach to gene inhibition because now transcripts can be altered to encode proteins or RNAs which can inhibit the function of the targeted gene. In other words, with targeted trans-splicing, deleterious transcripts can be turned against themselves.

As noted above, trans-splicing may also be accomplished without the use of ribozymes. It has been demonstrated that spliced leader sequences from lower eucaryotes can be trans-spliced onto mammalian 3' splice sites in tissue culture cells (J. P. Bruzik, T. Maniatis, Nature 360, 692 (1992)). Trans-splicing in this case is mediated by the spliceosome or splicing factors. Thus, it is possible to employ spliceosomes to alter the sequence of targeted transcripts for some desired end via targeted trans-splicing.

Thus, this invention provides a means for performing molecular reconstructive surgery. A defective part of a useful RNA molecule can be cut away from the rest of the molecule and subsequently replaced by a functional part. Alternatively, a functional portion of a disease-causing or deleterious RNA can be replaced by an inhibitory portion.

Administration

The above trans-splicing factors or agents can be administered by standard techniques, some of which are discussed below. They may be administered as RNA or expressed from expression vectors. Selected agents, e.g., oligonucleotides or ribozymes can be administered prophylactically, or to patients suffering from a target disease, e.g., by exogenous delivery of the agent to an infected tissue by means of an appropriate delivery vehicle, e.g., a liposome, a controlled release vehicle, by use of iontophoresis, electroporation or ion paired molecules, or covalently attached adducts, and other pharmacologically approved methods of delivery. Routes of administration include intramuscular, aerosol, oral (tablet or pill form), topical, systemic, ocular, intraperitoneal and/or intrathecal. Expression vectors for immunization with ribozymes and/or delivery of oligonucleotides are also suitable.

The specific delivery route of any selected agent will depend on the use of the agent. Generally, a specific delivery program for each agent will focus on naked agent uptake with regard to intracellular localization, followed by demonstration of efficacy. Alternatively, delivery to these same cells in an organ or tissue of an animal can be pursued. Uptake studies will include uptake assays to evaluate, e.g., cellular oligonucleotide uptake, regardless of the delivery vehicle or strategy. Such assays will also determine the intracellular localization of the agent following uptake, ultimately establishing the requirements for maintenance of steady-state concentrations within the cellular compartment containing the target sequence (nucleus and/or cytoplasm). Efficacy and cytotoxicity can then be tested. Toxicity will not only include cell viability but also cell function.

Some methods of delivery that may be used include:
a. encapsulation in liposomes,
b. transduction by retroviral vectors,
c. conjugation with cholesterol,
d. localization to nuclear compartment utilizing antigen binding site found on most snRNAs,
e. neutralization of charge of ribozyme by using nucleotide derivatives, and
f. use of blood stem cells to distribute ribozymes throughout the body.

At least three types of delivery strategies are useful in the present invention, including: ribozyme modifications, particle carrier drug delivery vehicles, and retroviral expression vectors. Unmodified ribozymes and antisense oligonucleotides, like most small molecules, are taken up by cells, albeit slowly. To enhance cellular uptake, the ribozyme may be modified essentially at random, in ways which reduce its charge but maintain specific functional groups required for RNA cleavage and splicing activity. This results in a molecule which is able to diffuse across the cell membrane, thus removing the permeability barrier.

Modification of ribozymes to reduce charge is just one approach to enhance the cellular uptake of these larger molecules. The random approach, however, is not advisable since ribozymes are structurally and functionally more complex than small drug molecules. The structural requirements necessary to maintain ribozyme catalytic activity are well understood by those in the art. (See, Cech, *Curr. Op. Structural Biol.*, 1992) These requirements are taken into consideration when designing modifications to enhance cellular delivery. The modifications are also designed to reduce susceptibility to nuclease degradation. Both of these characteristics should greatly improve the efficacy of the ribozyme. Cellular uptake can be increased by several orders of magnitude without having to alter the phosphodiester linkages necessary for ribozyme cleavage activity.

Chemical modifications of the phosphate backbone will reduce the negative charge thereby facilitating diffusion across the membrane. This principle has been successfully demonstrated for antisense DNA technology. The similarities in chemical composition between DNA and RNA make this a feasible approach. In the body, maintenance of an external concentration will be necessary to drive the diffusion of the modified ribozyme into the cells of the tissue. Administration routes which allow the diseased tissue to be exposed to a transient high concentration of the drug, which is slowly dissipated by systemic adsorption are preferred. Intravenous administration with a drug carrier designed to increase the circulation half-life of the ribozyme can be used. The size and composition of the drug carrier restricts rapid clearance from the blood stream. The carrier, made to accumulate at the site of infection, can protect the ribozyme from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver RNA to cells and that the RNA remains biologically active.

For example, a liposome delivery vehicle originally designed as a research tool, Lipofectin, has been shown to deliver intact mRNA molecules to cells yielding production of the corresponding protein.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system. Other controlled release drug delivery systems, such as nonoparticles and hydrogels may be potential delivery vehicles for a ribozyme. These carriers have been developed for chemotherapeutic agents and protein-based pharmaceuticals, and consequently, can be adapted for ribozyme delivery.

Topical administration of trans-splicing ribozymes is advantageous since it allows localized concentration at the site of administration with minimal systemic adsorption. This simplifies the delivery strategy of the ribozyme to the disease site and reduces the extent of toxicological characterization. Furthermore, the amount of material to be applied is far less than that required for other administration routes. Effective delivery requires the ribozyme to diffuse into the infected cells. Chemical modification of the ribozyme to neutralize negative charge may be all that is required for penetration. However, in the event that charge neutralization is insufficient, the modified ribozyme can be co-formulated with permeability enhancers, such as Azone or oleic acid, in a liposome. The liposomes can either represent a slow release presentation vehicle in which the modified ribozyme and permeability enhancer transfer from the liposome into the infected cell, or the liposome phospholipids can participate directly with the modified ribozyme and permeability enhancer in facilitating cellular delivery. In some cases, both the ribozyme and permeability enhancer can be formulated into a suppository formulation for slow release.

Such ribozymes may also be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal axed ophthalmic. Each of these administration routes expose the ribozyme to an accessible diseased tissue. Subcutaneous administration drains into a localized lymph node which proceeds through the lymphatic network into the circulation. The rate of entry into the circulation has been shown to be a function of molecular weight or size. The use of a liposome or other drug carrier localizes the ribozyme at the lymph node. The ribozyme can be modified to diffuse into the cell, or the liposome can directly participate in the delivery of either the unmodified or modified ribozyme to the cell.

A liposome formulation which can associate ribozymes with the surface of lymphocytes and macrophages is also useful. This will provide enhanced delivery to HIV-infected cells by taking advantage of the specificity of macrophage and lymphocyte immune recognition of infected cells. Whole blood studies show that the formulation is taken up by 90% of the lymphocytes after 8 hours at 37° C. Preliminary biodistribution and pharmacokinetic studies yielded 70% of the injected dose/gm of tissue in the spleen after one hour following intravenous administration.

Intraperitoneal administration also leads to entry into the circulation with the molecular weight or size of the ribozyme-delivery vehicle complex controlling the rate of entry.

Liposomes injected intravenously show accumulation in the liver, lung and spleen. The composition and size can be adjusted so that this accumulation represents 30% to 40% of the injected dose. The rest is left to circulate in the blood stream for up to 24 hours.

The chosen method of delivery will result in cytoplasmic accumulation in the afflicted cells and molecules should have some nuclease-resistance for optimal dosing. Nuclear delivery may be used but is less preferable. Most preferred delivery methods include liposomes (10–400 nm), hydrogels, controlled-release polymers, microinjection or electroporation (for ex vivo treatments) and other pharmaceutically applicable vehicles. The dosage will depend upon the disease indication and the route of administration but should be between 100–200 mg/kg of body weight/day. The duration of treatment will extend through the course of the disease symptoms, usually at least 14–16 days and possibly continuously. Multiple daily doses are anticipated for topical applications, ocular applications and vaginal applications. The number of doses will depend upon disease delivery vehicle and efficacy data from clinical trials.

Establishment of therapeutic levels of ribozyme within the cell is dependent upon the rate of uptake and degradation. Decreasing the degree of degradation will prolong the intracellular half-life of the ribozyme. Thus, chemically modified ribozymes, e.g., with modification of the phosphate backbone, or capping of the 5' and 3' ends of the ribozyme with nucleotide analogs may require different dosaging. Descriptions of useful systems are provided in the art cited above, all of which is hereby incorporated by reference herein.

Particular diseases that may be treated in this manner include any disease which can be treated by such RNAs, for example, HSV, HBV, EBV, and HIV infection; as well as various carriers (where the target molecule is located in a known cellular compartment).

Any disease caused by a specific set of mutations in a given genes RNA is potentially treatable by using target trans-splicing to correct such defective RNAs. Such diseases would include:

A. β-globin diseases (such as sickle cell anemia), cystic fibrosis, as well as any other genetic diseases caused by a point mutations or deletions in RNA.

B. Cancers caused by specific mutant oncogene encoding RNAs (e.g. bcr-abl mRNAs, mutant p53 mRNAs).

C. Genetic diseases caused by unstable trinucleotide repeats in RNAs (e.g. Huntington's disease, fragile X syndrome).

Other embodiments are within the following claims.

The invention claimed is:

1. Method for splicing a target RNA molecule comprising a mutant p53 nucleotide sequence within a cell in culture with a separate RNA molecule comprising a wild type p53 nucleotide sequence, wherein a protein product of the target RNA molecule is deleterious to the cell in which it is located, and wherein the separate RNA molecule is adapted to form a target RNA molecule with the wild type p53 nucleotide sequence in place of mutant p53 nucleotide sequence when spliced with at least a part of the target RNA molecule, the method comprising:

contacting the target RNA molecule with a catalytic RNA molecule comprising the separate RNA molecule, under conditions in which at least a portion of the separate RNA molecule is spliced with at least a portion of the target RNA molecule to form the target RNA molecule with the wild type p53 nucleotide sequence in place of mutant p53 nucleotide sequence when spliced with at least a part of the target RNA molecule.

2. The method of claim 1, wherein the catalytic RNA molecule is active to cleave the target RNA molecule comprising a mutant p53 nucleotide sequence and to splice the separate RNA molecule with the target RNA molecule comprising a mutant p53 nucleotide sequence.

3. The method of claim 1, wherein the contacting is in vitro.

4. The method of claim 3, wherein the contacting comprises providing a vector encoding the catalytic RNA molecule, wherein the catalytic RNA molecule includes the separate RNA molecule comprising a wild-type p53 nucleotide sequence.

5. The method of claim 1, wherein the catalytic RNA molecule is derived from a group I or group II intron molecule.

* * * * *